(12) United States Patent
Vogt

(10) Patent No.: US 6,322,357 B1
(45) Date of Patent: Nov. 27, 2001

(54) TELESCOPING FLEXIBLE BITE JUMPING DEVICE

(76) Inventor: William Vogt, 3501 Freemansburg Ave., Easton, PA (US) 18045

( * ) Notice: Subject to any disclaimer, the term of this patent is extended or adjusted under 35 U.S.C. 154(b) by 0 days.

(21) Appl. No.: 09/717,243

(22) Filed: Nov. 22, 2000

(51) Int. Cl.⁷ .................................................. A61C 3/00
(52) U.S. Cl. ........................................................ 433/19
(58) Field of Search ................................................ 433/19

(56) References Cited

U.S. PATENT DOCUMENTS

| | | | |
|---|---|---|---|
| 3,618,214 | 11/1971 | Armstrong | 433/19 |
| 3,798,773 | 3/1974 | Northcutt | 433/19 |
| 4,708,646 | 11/1987 | Jasper | 433/19 |
| 4,795,342 | 1/1989 | Jones | 433/19 |
| 5,562,445 | * 10/1996 | DeVincenzo et al. | 433/19 |
| 5,620,321 | * 4/1997 | Thornburg et al. | 433/19 |
| 5,711,667 | * 1/1998 | Vogt | 433/19 |
| 6,113,390 | 9/2000 | Sirney et al. | 433/19 |

* cited by examiner

Primary Examiner—John J. Wilson
(74) Attorney, Agent, or Firm—Gregory J. Gore

(57) ABSTRACT

An orthodontic appliance for moving the upper teeth relative to lower teeth in either a backward or a forward direction contains a resilient body coupled to at least one rotating end portion that allows the device to spin freely. Since the ends of the device spin freely, the stress of twisting on the flexible portion will be eliminated thus reducing breakage. Furthermore, the need for a different right and left device is eliminated. In addition, the end portion may also be telescoping in order to make the device expandable, thus allowing the patient to open his/her mouth more fully which results in the additional benefit of less appliance breakage. Also, because the device is expandable, the flexible portion can be made one size that will result in a more consistent force output and reduce the number of parts needed to manufacture the appliance.

6 Claims, 1 Drawing Sheet

TELESCOPING FLEXIBLE BITE JUMPING DEVICE

FIELD OF THE INVENTION

The present invention relates to an orthodontic intraoral force module which is used to correct the position of the upper teeth relative to the lower teeth in an anterior-posterior direction.

BACKGROUND OF THE INVENTION AND PRIOR ART

A majority of malocclusions involve some discrepancy in the position of the upper teeth relative to the lower teeth. Either the upper or lower teeth may be protruded or retruded relative to each other. Because these types of malocclusion cannot be corrected by braces alone, different types of force modules have been used that attach to the patient's braces that in conjunction with the braces deliver the proper force to correct these problems. Until fairly recently these force modules have consisted mainly of headgear and elastics, which are placed onto the braces by the patient. Unfortunately, the lack of patient cooperation in wearing removable devices severely limits the predictability of their results.

More recently, intraoral devices that connect to the patient's braces have been introduced. These devices eliminate the need for patient cooperation, however they introduce other problems. There are two types of these interarch devices; the rigid piston rod and cylinder type and the flexible spring type. Relevant issued patents of which the inventor is aware include U.S. Pat. Nos. 5,752,823; 5,562,445; 3,798,773, 4,708,646; and U.S. Pat. No. 5,435,721. The rigid type devices disclosed in these patents have the advantage of being more durable but they are bulkier and interfere with normal oral function. The patient better tolerates the flexible type but they are more prone to breakage and they limit the patient's range of jaw motion.

Therefore, although there are a variety of interarch devices for correcting anterior-posterior tooth discrepancies, there is a continued need in the art to improve existing options and to provide new devices that function more reliably while increasing patient comfort.

SUMMARY OF THE INVENTION

The present invention provides an orthodontic appliance designed to move the upper teeth relative to the lower teeth in a forward or backward direction to result in a bite correction between the upper and lower teeth. The device contains a resilient body coupled with at least one rotating end portion that allows the device to spin freely. The advantage is that since the ends can spin freely, the stress of twisting on the flexible part will be eliminated thus reducing breakage. Also, the need for a different right and left device can be eliminated, thereby reducing inventory. In addition, this end portion may be telescoping in order to make the device expandable, thus allowing for the patient to open his/her mouth more fully which results in a second benefit of less appliance breakage. Another advantage is that by having the device be expandable, the flexible portion can be one size. This will result in a more consistent force output level and reduce the amount of parts needed to manufacture the appliance.

More specifically, the applicant has invented an orthodontic device for applying forces between appliances affixed to the upper and lower teeth of the patient. A central flexible portion includes a cylindrical body having an internal axial bore. The body portion is laterally deflectable and resiliently biased toward axial alignment of the portion. A pair of rotating, telescoping end rods extend axially from opposite ends of the body and extend internally into it. Two end caps are affixed to opposite ends of the body and each includes an internal wall and axial alignment with the bore of the body. The walls provide means for slidably engaging each of the rods. At the end of the attachment rods are hooks for engaging an orthodontic appliance attached to a patient's tooth. The flexible central portion is preferably a coil spring. In an alternate embodiment attachment rods may be blocked against telescoping axial movement but retain their ability to freely rotate within the end caps of the central portion.

DESCRIPTION OF THE PREFERRED EMBODIMENT

Figure 1:
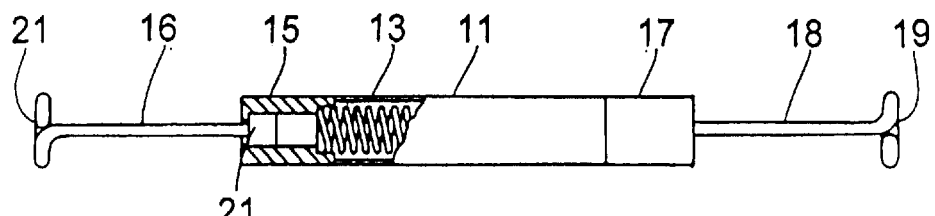
FIG. 1 is a side view of the orthodontic appliance of the present device in a patient's mouth.

Referring now to FIG. 1, the orthodontic device 11 consists of a flexible portion 13 and is composed of a closed coil spring 23 to which two end caps 15 and 17 are attached by way of inner threads. Two telescoping attachment rods 16 and 18 are slidably connected to the end caps. The rods are both rotatable and extendable. The rods have at their ends crimpable shepherd's hooks 19 and 21 shown in this figure for attaching to the patient's upper and lower braces. Although the coil spring is preferred, the flexible portion could alternatively be made of a flexible tube or filament. As shown in FIG. 1, the present invention is in its state of maximum extension.

Figure 2:
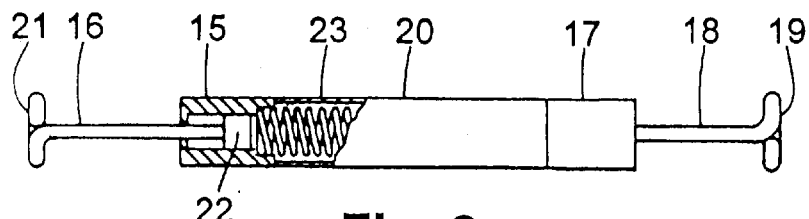
FIG. 2 is a partly sectioned side view of the present invention shown in isolation with its telescoping end rods in their extended position.
Figure 3:
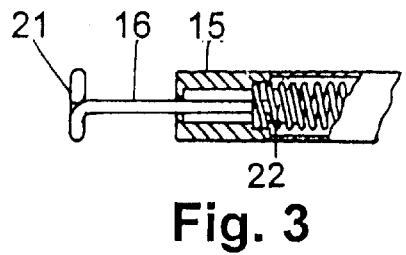
FIG. 3 is a partly sectioned side view of the present invention with the telescoping end rods shown retracted.

Referring now to FIGS. 2 and 3, the present invention is shown with the telescoping rods in their extended and retracted states respectively. As depicted in FIG. 2, the attachment rod 16 has a piston element 22 which resides within the coil spring 23 This element provides a slidable fit within the inner wall of the coil spring. A similar internal construction is found at the opposite end of the appliance with respect to attachment rod 18 and coil spring 23. FIG. 3 is similar to FIG. 2 except that the same parts are shown with the end rods in their retracted position. The inside diameter of coil spring is the same as the inner wall diameter of the cap so that the piston will be easily received within the coil spring as the end rods retract. A thin sheath 20 may be employed to cover the windings of the coil spring. Shepherd's hooks 19 and 21 are formed at the ends of the attachment rods to provide rotatable attachment to the appliances.

Figure 4:
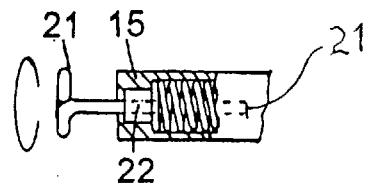
FIG. 4 is a partly sectioned side view of an alternate embodiment of the present invention.

Referring now to FIG. 4 in an alternate embodiment of the present invention, the end rods may be freely telescoping within a bore of piston element 22. In this embodiment, the piston element 22 is trapped between the end of the spring and a flange at the end of the cap. The piston thus remains stationary and the end rod is free to extend or retract as well as rotate. This embodiment provides advantages of the embodiment shown in FIGS. 1 through 3, however without the requirement that the inside diameter of the cap be matched to the inside diameter of the coil spring. This feature which permits the rods to rotate within the pistons may also be incorporated into the embodiment shown in FIGS. 1–3, if desired.

Figure 5:
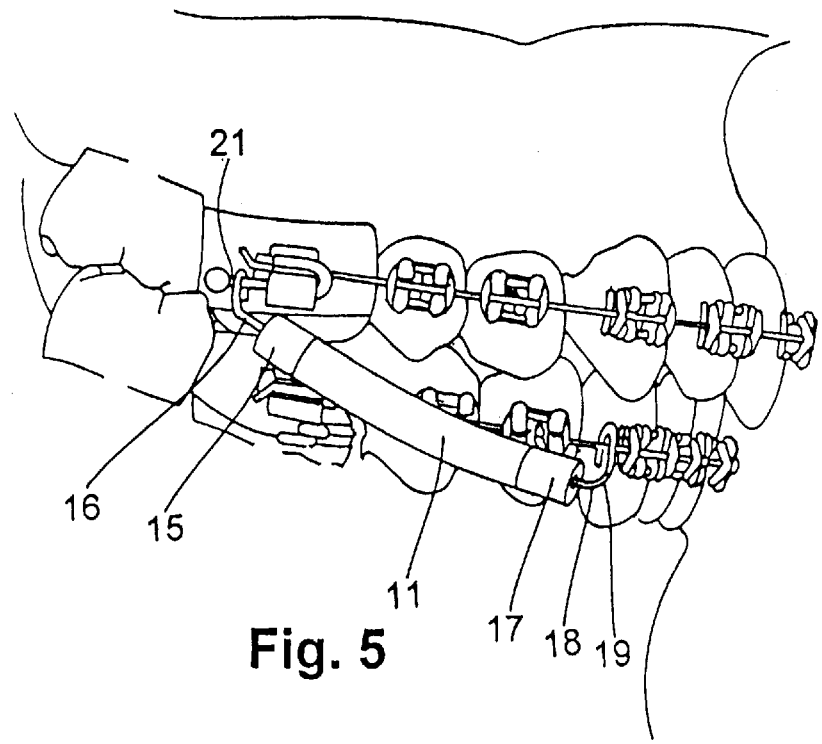
FIG. 5 is a view of the present invention worn by a patient.

Referring now to FIG. 5, the present orthodontic device is shown worn by a patient attached between the upper and lower jaws, the device having at least one but preferably two freely rotatable ends 19 and 21 allowing the patient to chew more easily while putting less stress on the device. Also, the attachment rods are telescoping within end caps 15 and 17 so that the device can be lengthened to allow for greater jaw opening and to accommodate different size mouths. The flexible portion 11 is straight when the patient's mouth is open but flexes on mouth closing so that a force is delivered to rods 16 and 18 and in turn, to the appliances they abut. This force then displaces the upper teeth relative to the lower teeth to effect a bite correction.

From the foregoing explanation it will be readily apparent that the present orthodontic appliance described herein has a flexible portion for patient comfort and it also has rotatable end attachments that are able to spin freely which increases the device's durability by eliminating stress due to twisting. Furthermore, the telescoping of the attachment rods allows for greater jaw opening. Thus, the objects of the invention and the needs in the art described above have been fulfilled. It should be understood that there may be other modifications and changes to the present invention that will be obvious to those of skill in the art from the foregoing description, however, the present invention should be limited only by the following claims and their legal equivalents.

What is claimed is:

1. An interarch orthodontic device for applying forces between an appliance affixed to the upper teeth and the second appliance affixed to the lower teeth of a patient, comprising:

a flexible central portion comprising an elongate cylindrical body having an internal axial bore, said resilient body being laterally deflectable and resiliently biased toward axial alignment thereof;

two end caps affixed to opposite ends of said central portion, said end caps each including a cylindrical internal wall in axial alignment with said central portion bore for slidably engaging each of said attachment rods;

a pair of rotatable attachment rods axially extending from end caps, said end rods each including a piston head at an interior end thereof, said piston head being in slideable and rotatable engagement with said internal walls of said end caps; and an attachment hook located at an exterior end of each of said attachment rods for engaging an orthodontic appliance attached to a patient's tooth.

2. The orthodontic device of claim 1 wherein said flexible central portion is a coil spring.

3. The orthodontic device of claim 2 wherein said end caps are affixed to said coil spring by threaded attachment.

4. The orthodontic device of claim 3 wherein said attachment hooks are shepherd type hooks providing freely rotatable attachment between said rods and said appliances.

5. The orthodontic device of claim 1 wherein each of said attachment rod pistons is axially extensible into said bore of said central flexible portion.

6. The orthodontic device of claim 1 further described in that each of said attachment rods is slideable within said pistons.

* * * * *